(12) United States Patent
Tan

(10) Patent No.: US 8,441,651 B2
(45) Date of Patent: May 14, 2013

(54) DEFECT INSPECTION APPARATUS AND DEFECT INSPECTION METHOD

(75) Inventor: Xiaodi Tan, Saitama (JP)

(73) Assignee: Sony Corporation, Tokyo (JP)

( * ) Notice: Subject to any disclaimer, the term of this patent is extended or adjusted under 35 U.S.C. 154(b) by 411 days.

(21) Appl. No.: 12/869,942

(22) Filed: Aug. 27, 2010

(65) Prior Publication Data

US 2011/0058160 A1 Mar. 10, 2011

(30) Foreign Application Priority Data

Sep. 4, 2009 (JP) ................................. 2009-204491

(51) Int. Cl.
*G01B 11/02* (2006.01)
*G01N 21/00* (2006.01)

(52) U.S. Cl.
USPC ........................................ 356/512; 356/237.2

(58) Field of Classification Search ........... 356/512–515
See application file for complete search history.

(56) References Cited

U.S. PATENT DOCUMENTS

| 6,433,339 | B1 * | 8/2002 | Maeda et al. ............... | 250/341.4 |
| 6,879,390 | B1 * | 4/2005 | Kvamme et al. ............ | 356/237.2 |
| 7,583,386 | B2 * | 9/2009 | Freischlad et al. ............ | 356/497 |
| 7,911,601 | B2 * | 3/2011 | Uto et al. ..................... | 356/237.5 |
| 2008/0094616 | A1 * | 4/2008 | Tanaka ......................... | 356/237.2 |

FOREIGN PATENT DOCUMENTS

| JP | 2006-516737 | 7/2006 |
| JP | 2006-208196 | 8/2006 |

* cited by examiner

*Primary Examiner* — Michael A Lyons
(74) *Attorney, Agent, or Firm* — Dentons US LLP

(57) ABSTRACT

Disclosed herein is a defect inspection apparatus including: a light source for emitting laser light; a mirror group for splitting the wave surface of incident laser light emitted by the light source into a plurality of component wave surfaces, arranging the component wave surfaces to form an array oriented in one direction and aligning the component wave surfaces to form a single wave surface after propagating the laser light through a moving object of measurement; an interferometer for splitting the single wave surface into two partial wave surfaces to create an interference stripe; an imaging section for taking an image of the interference stripe created by the interferometer; and an analysis section for detecting a defect existing on the surface of the moving object of measurement on the basis of changes of the image, which has been taken as the image of the interference stripe, with the lapse of time.

8 Claims, 13 Drawing Sheets

PRIOR ART FIG. 2A
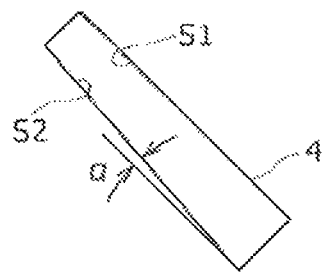
PRIOR ART FIG. 2B
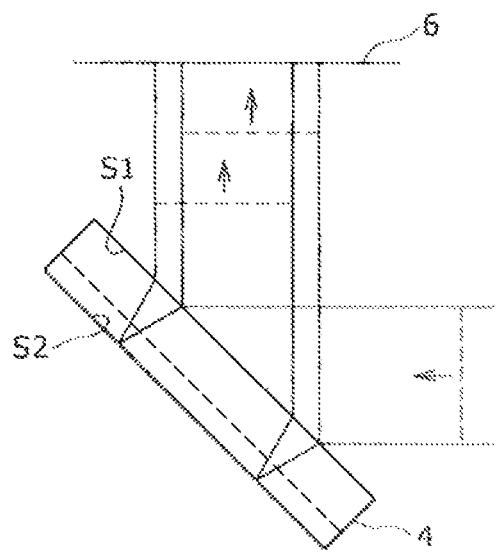
PRIOR ART FIG. 2C
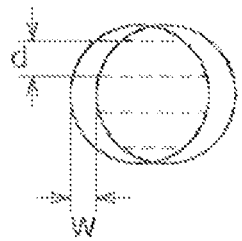

PRIOR ART  FIG. 3A
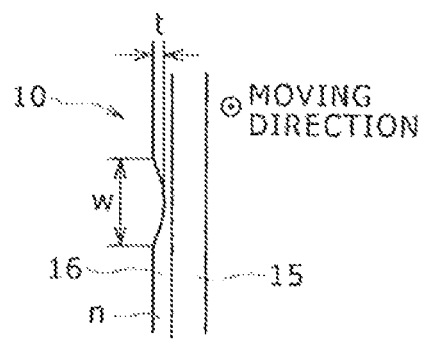
PRIOR ART  FIG. 3B
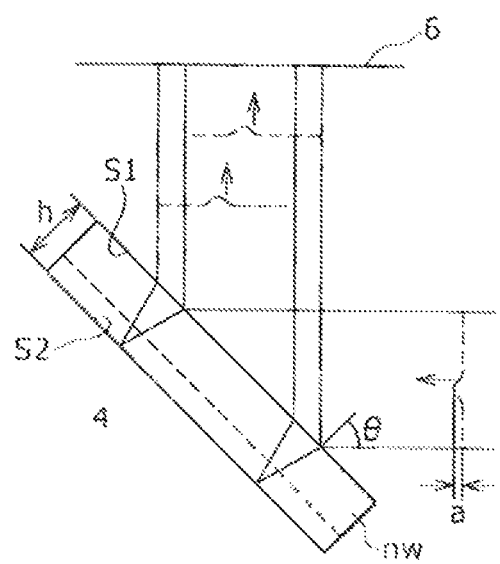
PRIOR ART  FIG. 3C
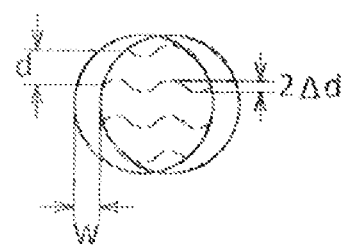

PRIOR ART FIG. 4A
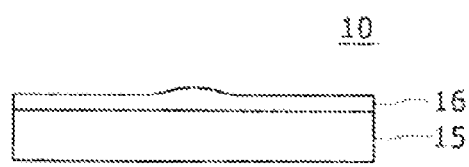
FIG. 4B
PRIOR ART
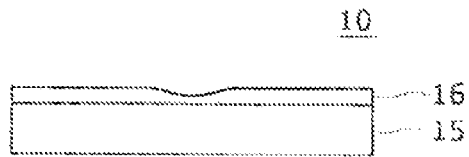

F I G. 7
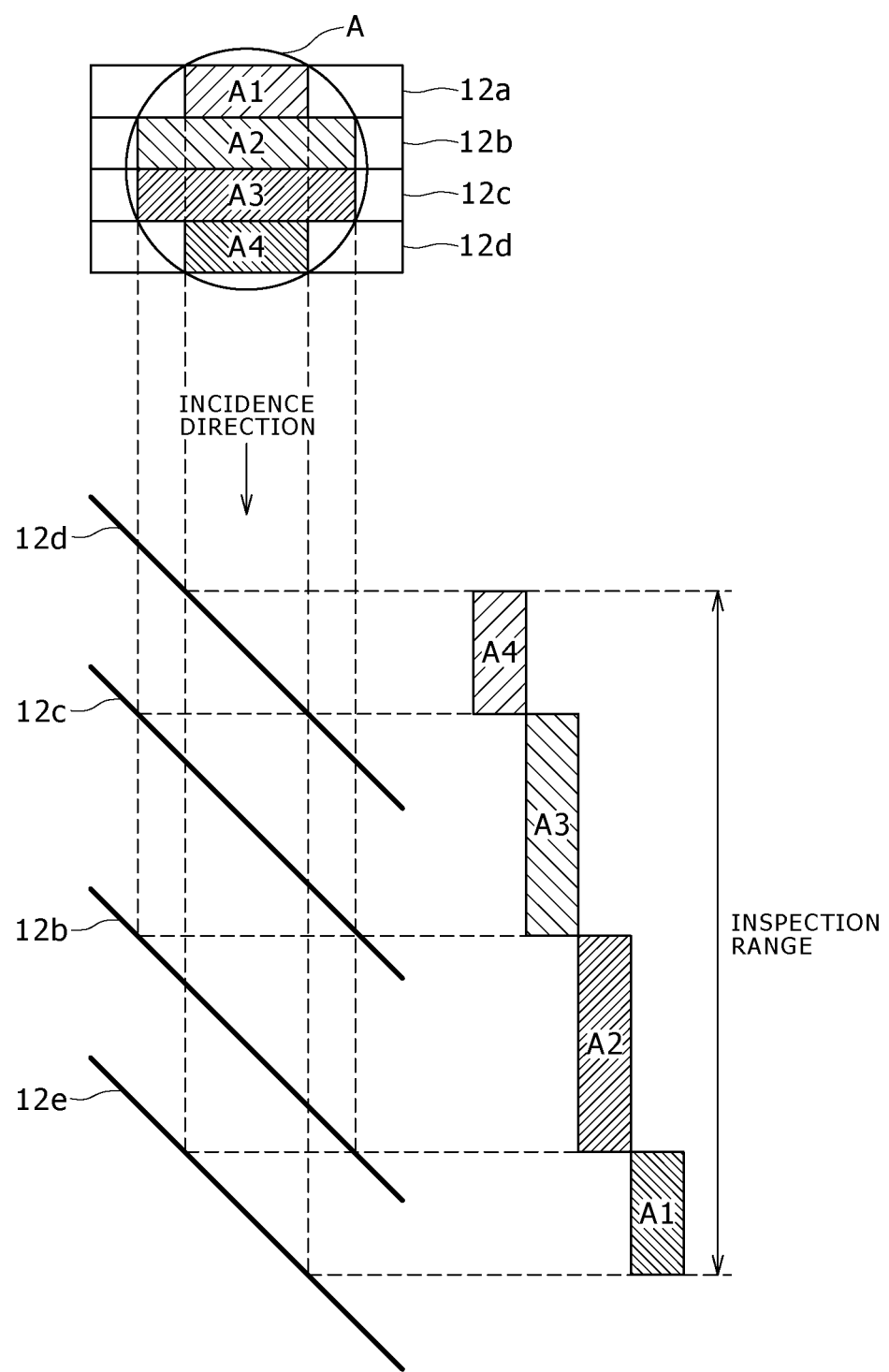

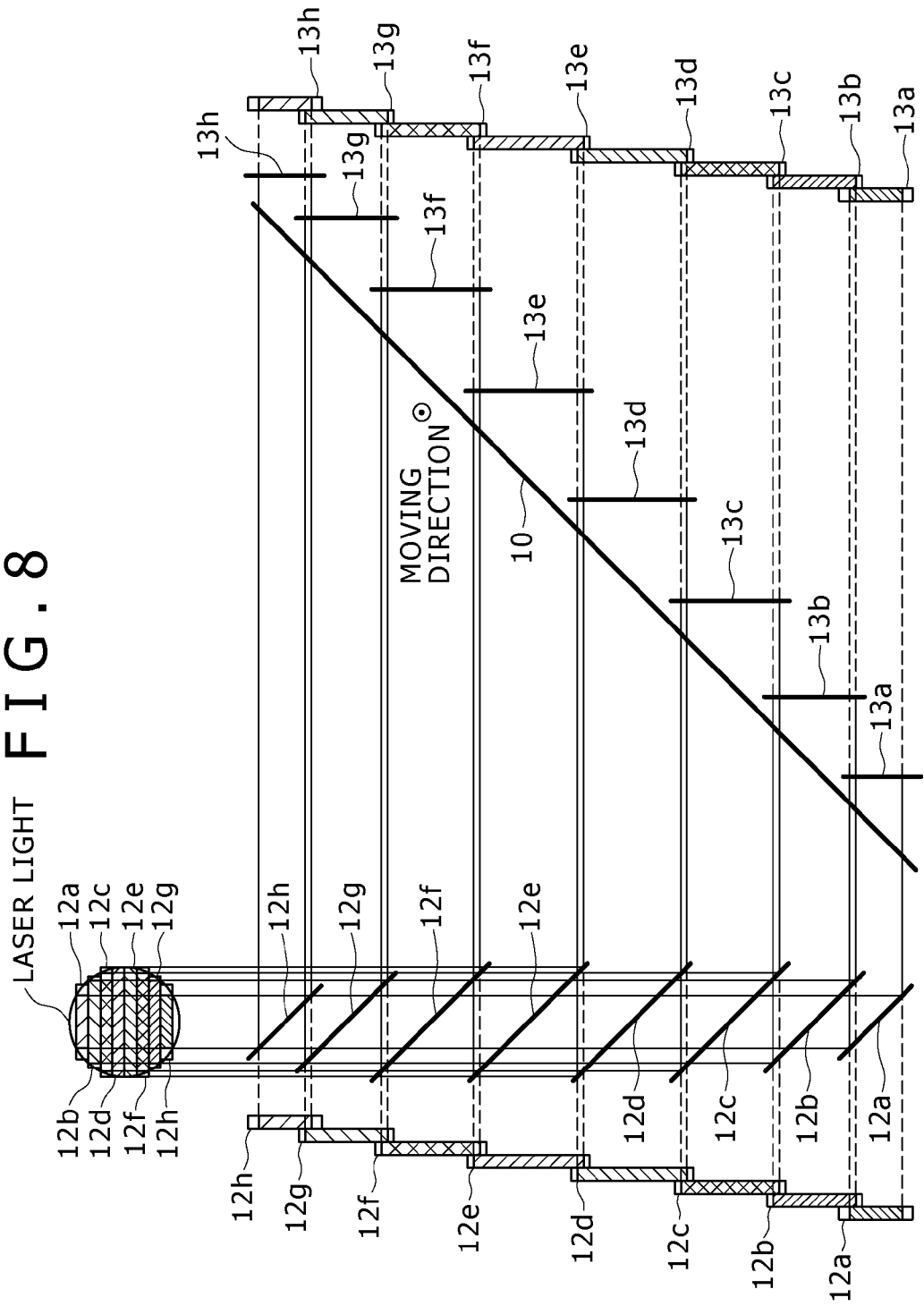

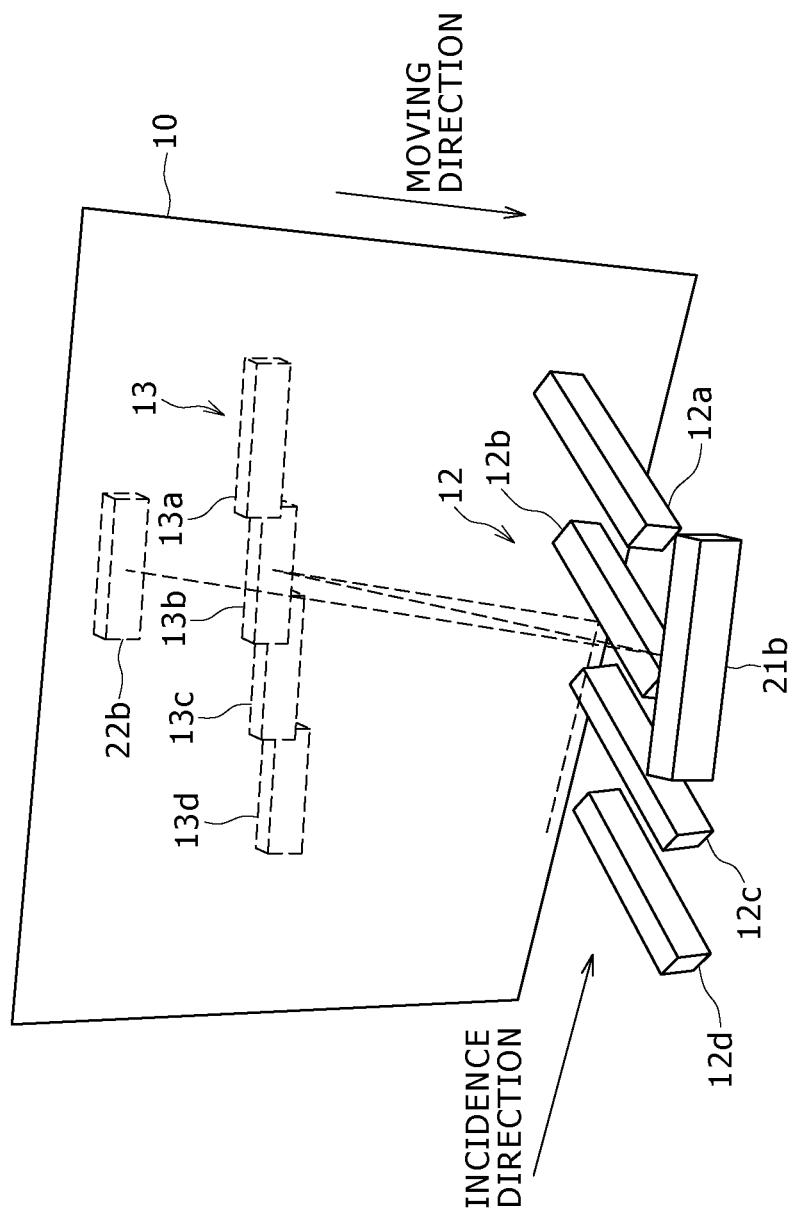

DEFECT INSPECTION APPARATUS AND DEFECT INSPECTION METHOD

BACKGROUND OF THE INVENTION

1. Field of the Invention

The present invention relates to a defect inspection apparatus for detecting a defect of a measurement object such as an optical film and also relates to a defect inspection method adopted by the defect inspection apparatus.

2. Description of the Related Art

In recent years, a liquid-crystal display apparatus has been becoming very popular as a display apparatus representing television receiver sets and PCs (Personal Computers). The liquid-crystal display apparatus employs one of a variety of optical films to serve as the surface of a polarization plate. A main example of the optical films is a TAC (Tri-acetyl cellulose) film. In general, the optical film such as the TAC film is flexible and prone to injury. Thus, a hard coat layer 16 is typically created on the surface of a TAC film 15 as shown in FIG. 13, in order to improve the characteristic of being proof against strikes which may cause injuries. As shown in FIG. 14A, a hard coat layer 16 is laid on the surface of the TAC film 15 serving as the original film in a direction referred to as a moving direction. In order to lay a hard coat layer 16 on the surface of the TAC film 15, a coating section such as a blade 110 is used to apply a hard coat material continuously to the surface of the TAC film 15. When the hard coat material applied to the surface of the TAC film 15 hardens, a hard coat layer 16 is created on the surface of the TAC film 15.

While the hard coat material is being applied continuously to the surface of the TAC film 15, however, a portion of the coating section such as the blade 110 may be clogged up in some cases as shown by a mark X at a position P in FIG. 14B. Thus, coating unevenness is formed to have a line shape oriented in the moving direction of the blade 110 over the surface of the TAC film 15 as shown in FIG. 14B. As a result, after the hard coat material applied to the surface of the TAC film 15 hardens, a cord having a fixed length and a line shape oriented in the moving direction of the blade 110 over the surface of the TAC film 15 may be left in some cases on the hard coat layer 16 laid on the surface of the TAC film 15. If such a TAC film 15 is used in a light polarization device, the display characteristic of a liquid-crystal display apparatus employing the light polarization device may be badly affected in some cases so that improvement is desired.

By the way, there has been proposed a system to serve as a system based on an existing technology for acquiring information on a microstructure or information on the structure of the surface of a physical body such as a panel, a substrate or a wafer. The proposed system makes use of a sharing interferometer for splitting the wave surface of light radiated to an object of measurement into two partial wave surfaces and letting the two partial wave surfaces interfere with each other. For more information on the proposed system, the reader is advised to refer to documents such as Japanese Patent Laid-Open No. 2006-516737 (hereinafter referred to as Patent Document 1).

In addition, there has also been proposed a method to be used as a method for detecting a defect of an optical film which serves as an object of measurement. In accordance with the proposed method, an image of the optical film is taken by making use of typically a CCD (Charge Coupled Devices) camera and a defect of the optical film is detected by detecting color-tone changes or shading changes. For more information on the proposed method, the reader is advised to refer to documents such as Japanese Patent Laid-Open No. 2006-208196 (hereinafter referred to as Patent Document 2).

SUMMARY OF THE INVENTION

In the system disclosed in Patent Document 1 described above, however, it is difficult to detect the existence of a defect over a wide range stretched in the width direction of an optical film during a manufacturing process. In addition, this system makes use of a technology for detecting the existence of a defect on an object of measurement on the basis of light reflected by the surface of the object of measurement. Patent Document 1 also does not describe detection of a defect existing on an optical film which has a good light transmission characteristic. A typical example of the optical film having a good light transmission characteristic is the TAC film described above.

In addition, in accordance with the defect detection method disclosed in Patent Document 2 described above, it is difficult to observe a wide range of an optical film which is moving.

Addressing the problems described above, inventors of the present invention have proposed a defect inspection apparatus for detecting a defect over a wide range on a measurement object and also relates to a defect inspection method adopted by the defect inspection apparatus.

In order to solve the problems described above, in accordance with a first embodiment of the present invention, there is provided a defect inspection apparatus which employs: a light source for emitting laser light; a mirror group for splitting the wave surface of incident laser light emitted by the light source into a plurality of component wave surfaces, arranging the component wave surfaces to form an array oriented in one direction and aligning the component wave surfaces to form a single wave surface after propagating the laser light through a moving object of measurement; an interference plate for splitting the single wave surface into two partial wave surfaces and making use of the two partial wave surfaces to create an interference stripe; an imaging section for taking an image of the interference stripe created by the interference plate; and an analysis section for detecting a defect existing on the surface of the moving object of measurement on the basis of changes of the image, which has been taken by the imaging section as the image of the interference stripe, with the lapse of time.

In order to solve the problems described above, in accordance with a second embodiment of the present invention, there is provided a defect inspection method which includes the steps of: driving a light source to emit laser light; driving a mirror group to split the wave surface of incident laser light emitted by the light source into a plurality of component wave surfaces, arranging the component wave surfaces to form an array oriented in one direction and aligning the component wave surfaces to form a single wave surface after propagation of the laser light through a moving object of measurement; splitting the single wave surface into two partial wave surfaces and making use of the two partial wave surfaces to create an interference stripe; taking an image of the created interference stripe; and detecting a defect existing on the surface of the moving object of measurement on the basis of changes of the taken image of the interference stripe with the lapse of time.

As described above, in accordance with the first and second embodiments of the present invention, the light source is used for emitting laser light whereas the mirror group is used for splitting the wave surface of incident laser light emitted by the light source into a plurality of component wave surfaces, arranging the component wave surfaces to form an array oriented in one direction and aligning the component wave surfaces to form a single wave surface after propagating the laser light through a moving object of measurement. When the laser light having its wave surface split into the component wave surfaces passes through the moving object of measurement, the wave surface of the laser light may rumple due to a defect possibly existing on the surface of the measurement object. Then, after the laser light has passed through the moving object of measurement, the mirror group aligns the component wave surfaces to form a single wave surface. Then, the interference plate is used for splitting the single wave surface into two partial wave surfaces and making use of the two partial wave surfaces to create an interference stripe. Subsequently, the imaging section is used for taking an image of the interference stripe created by the interference plate. Finally, the analysis section is used for detecting a defect existing on the surface of the moving object of measurement on the basis of changes of the image, which has been taken by the imaging section as the image of the interference stripe, with the lapse of time. As a result, it is possible to detect a defect existing on the surface of the moving object of measurement in a wide range extended in the width direction of the measurement object.

As described above, in accordance with the present invention, it is possible to detect a defect of a measurement object over a wide range stretched in the width direction of the measurement object.

BRIEF DESCRIPTION OF THE DRAWINGS

FIG. 2A is a diagram showing a typical shape of the wedge plate;

FIG. 2B is a diagram to be referred to in description of the principle of generation of an interference stripe for a case in which an optical film has no defects;

FIG. 2C is a diagram showing a typical interference stripe for a case in which an optical film has no defects;

FIG. 3A is an explanatory diagram roughly showing a typical defect generated on an optical film;

FIG. 3B is an explanatory rough diagram to be referred to in description of the principle of generation of an interference stripe for a case in which the optical film has a defect;

FIG. 3C is an explanatory diagram roughly showing a typical interference stripe for a case in which the optical film has a defect;

FIG. 4A is a diagram roughly showing the optical film having a protrusion which is a typical defect;

FIG. 4B is a diagram roughly showing the optical film having a dent which is another typical defect;

FIG. 7 is a diagram showing relations between the first mirrors and the rectangular wave surfaces split by the first mirrors;

FIG. 8 is a rough diagram to be referred to in description of a process to split the wave surface of laser light into a plurality of component wave surfaces;

FIG. 11 is a diagram roughly showing a typical layout of first to fourth mirrors in accordance with a second embodiment of the present invention;

DETAILED DESCRIPTION OF THE PREFERRED EMBODIMENTS

Preferred embodiments of the present invention are explained by referring to diagrams in chapters which are arranged as follows.
1: Principle of Detection of Defects on an Optical Film
2: First Embodiment (Embodiment Employing First and Second Mirror Groups)
3: Second Embodiment (Embodiment Employing Also Third and Fourth Mirror Groups)

1: Principle of Detection of Defects on an Optical Film

First of all, in order to make the explanation of embodiments of the present invention easy to understand, the following description explains the principle of detection of a defect existing on an optical film 10 through the use of a sharing interferometer.
[Configuration of the Defect Inspection Apparatus]

Figure 1:
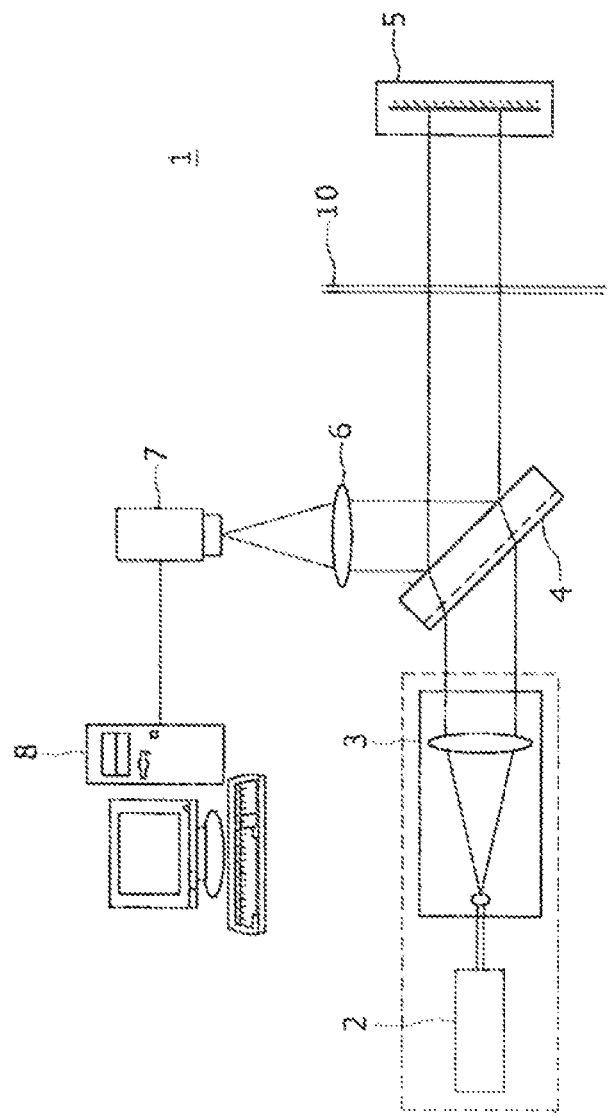
FIG. 1 is a diagram roughly showing a typical configuration of a defect inspection apparatus.

FIG. 1 is a diagram showing a typical configuration of a defect inspection apparatus 1. As shown in FIG. 1, the defect inspection apparatus 1 employs a light source 2, a beam expander 3, a wedge plate 4, a mirror 5, an image creation lens 6, an imaging section 7 and an analysis section 8. An optical film 10 serving as the object of measurement is placed between the wedge plate 4 and the mirror 5. The optical film 10 typically includes an optical film such as a TAC film 15 and another optical film created on the TAC film 15 such as a hard coat layer 16.

The light source 2 emits laser light which serves as coherent light to the beam expander 3. The beam expander 3 expands the wave surface of the incident laser light coming from the light source 2 to a magnitude determined in advance. The beam expander 3 then directs the laser light to the wedge plate 4 as parallel laser light beams.

The wedge plate 4 is provided by being oriented in a direction which is inclined with respect to the direction of the incident laser light beams coming from the beam expander 3 to form an angle determined in advance in conjunction with the direction of the laser light beams. The wedge plate 4 transmits the laser light beams coming from the beam expander 3 to the mirror 5 for reflecting the laser light beams. The wedge plate 4 also splits the wave surface (a detected wave surface) of laser light reflected by the mirror 5 into two partial wave surfaces, provides a spatial displacement between the two partial wave surfaces and lets the two partial wave surfaces interfere with each other.

FIG. 2A is a diagram showing a typical shape of the wedge plate 4. As shown in FIG. 2A, the wedge plate 4 has a wedge shape. To put it more concretely, the wedge plate 4 has first and second surfaces S1 and S2 which face each other. The second surface S2 is inclined with respect to the first surface S1, forming a predetermined angle α in conjunction with the first surface S1.

In the wedge plate 4 having such a configuration, a part of the laser light reflected from the mirror 5 is reflected by the first surface S1 to the image creation lens 6. On the other hand, the rest of the laser light reflected from the mirror 5 is not reflected by the first surface S1 to the image creation lens 6. Instead, the rest of the laser light reflected from the mirror 5 propagates into the inside of the wedge plate 4 and arrives at the second surface S2. The second surface S2 then reflects the rest of the laser light.

The laser light transmitted by the wedge plate 4 from the beam expander 3 propagates to the mirror 5 by way of the optical film 10 which serves as an object of measurement. The mirror 5 reflects the laser light back to the wedge plate 4 also by way of the optical film 10. The mirror 5 is disposed perpendicularly to the incidence direction of the laser light form the wedge plate 4 thereby reflecting the incident laser light.

The image creation lens 6 creates an interference stripe, which has been formed by the wedge plate 4, on the imaging section 7 as an image. The imaging section 7 is typically a CCD (Charge Coupled Devices) camera. The imaging section 7 takes an image of the interference stripe which has been created by the image creation lens 6 on imaging devices employed in the imaging section 7. A typical example of the imaging devices is CCDs (Charge Coupled Devices). The imaging section 7 supplies the image of the interference stripe as image data to the analysis section 8. The analysis section 8 analyzes the image data received from the imaging section 7 as data of the interference stripe by adoption of a predetermined algorithm in order to detect a defect existing on the optical film 10.

[Operations of the Defect Inspection Apparatus]

The following description explains typical operations carried out by the defect inspection apparatus 1 having the configuration described above in order to detect a defect existing on the optical film 10. As described above, the light source 2 emits laser light to the beam expander 3. The beam expander 3 expands the wave surface of the incident laser light to a magnitude determined in advance. The beam expander 3 then directs the laser light to the wedge plate 4 as parallel laser light beams. The wedge plate 4 transmits the laser light to the mirror 5 for reflecting the laser light. The laser light transmitted by the wedge plate 4 propagates to the mirror 5 by way of the optical film 10. The mirror 5 reflects the laser light back to the wedge plate 4 also by way of the optical film 10.

FIG. 2B is a diagram showing the wedge plate 4 reflecting laser light. FIG. 2C is a diagram showing a typical interference stripe which has been formed by the wedge plate 4. As shown in FIG. 2B, the wedge plate 4 splits the wave surface of the laser light reflected by the mirror 5 back to the wedge plate 4 by way of the optical film 10 into two partial wave surfaces. To put it more concretely, a part of the laser light reflected from the mirror 5 is reflected by the first surface S1 of the wedge plate 4 to the image creation lens 6 as laser light with one of the partial wave surfaces. On the other hand, the rest of the laser light reflected from the mirror 5 is not reflected by the first surface S1 to the image creation lens 6. Instead, the rest of the laser light reflected from the mirror 5 propagates into the inside of the wedge plate 4 and arrives at the second surface S2. The second surface S2 then reflects the rest of the laser light, which has been reflected from the mirror 5, to the image creation lens 6 as laser light with the other partial wave surface.

By splitting the wave surface of the laser light arriving at the wedge plate 4 from the mirror 5 into two partial wave surfaces as described above, a spatial displacement is generated between the two partial wave surfaces. Then, by superposing the laser light having one of the two partial wave surfaces on the laser light having the other partial wave surface, an image of an interference stripe is created on the imaging section 7 as shown in FIG. 2C.

FIG. 2C is a diagram showing the partial wave surfaces for a typical interference stripe for a case in which the optical film 10 does not have a defect. An interference stripe pitch d can be expressed by Ex. (1) given below. In this equation, reference notation α denotes the wedge angle of the wedge plate 4 whereas reference notation λ denotes the wavelength of the laser light.

$$d = \frac{\lambda}{2\tan\alpha} = \text{constant} \tag{1}$$

The interference stripe formed by the wedge plate 4 is created as an image in the imaging section 7 which then converts the image into an electrical signal. The imaging section 7 subsequently supplies the electrical signal to the analysis section 8 as a signal representing image data. Finally, the analysis section 8 analyzes the image data received from the imaging section 7 as data of the interference stripe by adoption of a predetermined algorithm in order to detect a defect which may exist on the optical film 10.

[Detection of Defects on the Optical Film]

A typical defect detection method adopted by the analysis section 8 is explained by referring to diagrams of FIGS. 3A to 3C as follows. FIG. 3A is an explanatory diagram roughly showing a typical defect generated on an optical film 10 which is obtained by creating a hard coat layer 16 on the surface of a TAC film 15. The following description explains a defect detection method for detecting a typical defect generated on the hard coat layer 16. The typical defect generated on the hard coat layer 16 is a cord which has a dent shape. As shown in FIG. 3A, the dent has a width w oriented in the horizontal direction with respect to the moving direction of the optical film 10 and a depth t. However, the shape of a defect that can be detected by the defect inspection apparatus 1 is not limited to the typical shape shown in the explanatory diagram of FIG. 3A. For example, the defect inspection apparatus 1 is also capable of detecting a defect which is a cord having a protrusion shape.

If the optical film 10 has a defect like the one shown in the explanatory diagram of FIG. 3A, the wave surface of laser light passing through the defect is shifted from the wave surface of light passing through portions other than the defect. In this case, a wave surface is created, being bent to form a protrusion on a portion thereof as shown in FIG. 3B. As a result, the wave surface of the laser light rumples. The curvature width a of the bent wave surface is expressed by Ex. (2) as follows.

$$a = 2(n-1)t \tag{2}$$

Reference notations n and t used in the above equation denote the following quantities:
n: The refraction index of the hard coat layer 16
t: The depth of a defect created on the hard coat layer 16

When laser light reflected by the mirror 5 as laser light having such a wave surface arrives at the wedge plate 4, as shown in FIG. 3B, a part of the incident laser light reflected from the mirror 5 is reflected by the first surface S1 of the wedge plate 4 to the image creation lens 6 as laser light with one of the two partial wave surfaces. On the other hand, the rest of the laser light reflected from the mirror 5 is not reflected by the first surface S1 to the image creation lens 6. Instead, the rest of the laser light reflected from the mirror 5 propagates into the inside of the wedge plate 4 and arrives at the second surface S2. The second surface S2 then reflects the rest of the laser light, which has been reflected from the mirror 5, to the image creation lens 6 as laser light with the other partial wave surface. At that time, a spatial displacement is generated between the two partial wave surfaces, that is, the partial wave surface of the laser light reflected by the first surface S1 of the wedge plate 4 to the image creation lens 6 and the partial wave surface of the laser light reflected by the second surface S2 of the wedge plate 4 to the image creation lens 6. That is to say, the laser light reflected by the first surface S1 serves as the laser light having one of the two partial wave surfaces whereas the laser light reflected by the second surface S2 serves as the laser light having the other partial wave surface. Then, by superposing the laser light having one of the two partial wave surfaces on the laser light having the other partial wave surface, an image of an interference stripe is created on the imaging section 7 as shown in FIG. 3C.

As described above, when a cord is generated on the hard coat layer 16 of the optical film 10, an interference stripe having a wave shape is created. The interference stripe with a wave shape has a pitch d and a displacement $\Delta d$ which are correlated with the depth t of the cord generated on the hard coat layer 16 formed on the optical film 10. The depth t of the cord generated on the hard coat layer 16 formed on the optical film 10 is expressed by Ex. (3) given below. In Ex. (3), reference notation d denotes the pitch of the interference stripe, reference notation $\Delta d$ denotes the displacement of the interference stripe, reference notation n denotes the refraction index of the hard coat layer 16 whereas reference notation $\lambda$ denotes the wavelength of the laser light.

$$t = \frac{\Delta d}{2(n-1)d} \cdot \lambda \quad (3)$$

In addition, Ex. (4) given below expresses a spatial displacement W generated between the two partial wave surfaces. In Ex. (4), reference notation nw denotes the refraction index of the wedge plate 4, reference notation h denotes the thickness of the wedge plate 4 whereas reference notation $\theta$ denotes the incidence angle formed by the wedge plate 4 and the laser light incident on the wedge plate 4. It is to be noted that, in this typical expression, the thickness h of the wedge plate 4 is an average value of heights of the wedge plate 4 and the spatial displacement W generated between the two partial wave surfaces is greater than the width w of the cord generated on the hard coat layer 16 formed on the optical film 10.

$$w < W = \frac{2h \cdot \sin^2\theta}{\sqrt{n_W^2 - \sin^2\theta}} \quad (4)$$

As described above, the analysis section 8 analyzes the image data received from the imaging section 7 as data of the interference stripe by adoption of a predetermined algorithm in order to detect a defect which may probably exist on the optical film 10. If a defect has been generated on the optical film 10 for example, the displacement of curves created in the interference stripe is greater than the displacement of curves created for a case in which no defect has been generated on the optical film 10.

In the defect inspection apparatus 1 used in the explanation of the principle described above, the width of the laser-light wave surface expanded by the beam expander 3 becomes approximately the range of inspection of the optical film 10 for existence of a defect. On the other hand, the width of the optical film 10 also referred to as the original film serving as the object of measurement generally has a band shape. Thus, the defect inspection apparatus 1 is capable of inspecting only a small area of the moving optical film 10.

2: First Embodiment

Next, a first embodiment of the present invention is explained as follows. In the first embodiment of the present invention, a mirror group is used for splitting the circular-shaped wave surface of laser light into a plurality of component wave surfaces each having an approximately rectangular shape and the component wave surfaces are arranged in the width direction of the optical film 10 so as to allow defects to be detected over a wide range of the optical film 10.

[Optical Film]

Figure 13:
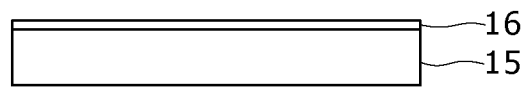
FIG. 13 is a diagram roughly showing a typical configuration of an optical film.
Figure 14A:
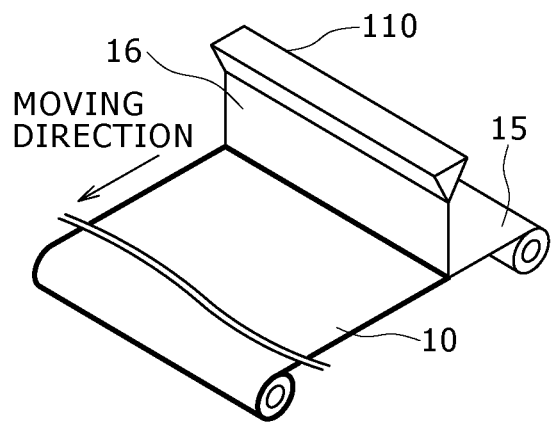
FIG. 14A is an explanatory diagram referred to in description of a process to manufacture an optical film with no defects generated.

First of all, the following description explains the optical film 10 which serves as the object of measurement in embodiments of the present invention. As described earlier, the optical film 10 is obtained by creating a hard coat layer 16 on the surface of a TAC film 15 as shown in FIG. 13. As shown in FIG. 14A which is an explanatory diagram referred to in description of a process to manufacture an optical film with no defects generated, a hard coat layer 16 is laid over the surface of the TAC film 15 serving as the original film in a direction referred to as a moving direction. In order to lay a hard coat layer 16 over the surface of the TAC film 15, a coating section such as a blade 110 is used to apply a hard coat material continuously to the surface of the TAC film 15. When the hard coat material applied to the surface of the TAC film 15 hardens, a hard coat layer 16 is created on the surface of the TAC film 15, forming the optical film 10.

Figure 14B:
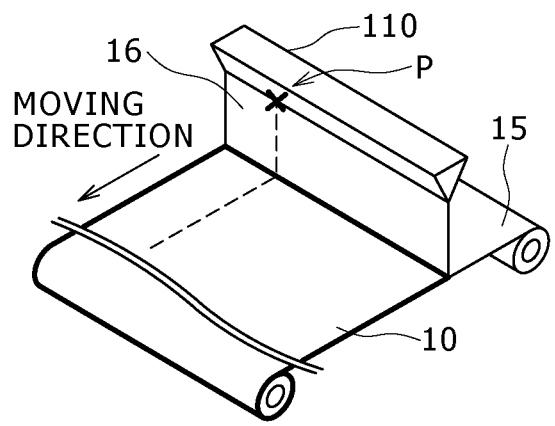
FIG. 14B is an explanatory diagram referred to in description of a process to manufacture an optical film with a defects generated.

While the hard coat material is being applied continuously to the surface of the TAC film 15, however, a portion of the coating section such as the blade 110 may be clogged up in some cases as shown by a mark X at a position P in FIG. 14B which is an explanatory diagram referred to in description of a process to manufacture an optical film with a defect generated. Thus, coating unevenness is formed to have a line shape oriented in the moving direction of the blade 110 over the surface of the TAC film 15 as shown in FIG. 14B. As a result, after the hard coat material applied to the surface of the TAC film 15 hardens, a cord having a fixed length and a line shape oriented in the moving direction of the blade 110 over the surface of the TAC film 15 may be left in some cases on the hard coat layer 16 laid on the surface of the TAC film 15.

To put it more concretely, let coating unevenness be formed to have a line shape oriented in the moving direction of the blade 110 over the surface of the TAC film 15 as shown in FIG. 14B. In this case, a cord having a line shape oriented in the moving direction of the blade 110 over the surface of the TAC film 15 is left on the hard coat layer 16 as a protrusion on a portion of the hard coat layer 16 as shown in FIG. 4A. As an alternative, a cord having a line shape oriented in the moving direction of the blade 110 over the surface of the TAC film 15 is left on the hard coat layer 16 as a dent on a portion of the hard coat layer 16 as shown in FIG. 4B. It is to be noted that the film used in the description given so far may also be interpreted as a sheet film.

[Configuration of the Defect Inspection Apparatus]

Figure 5:
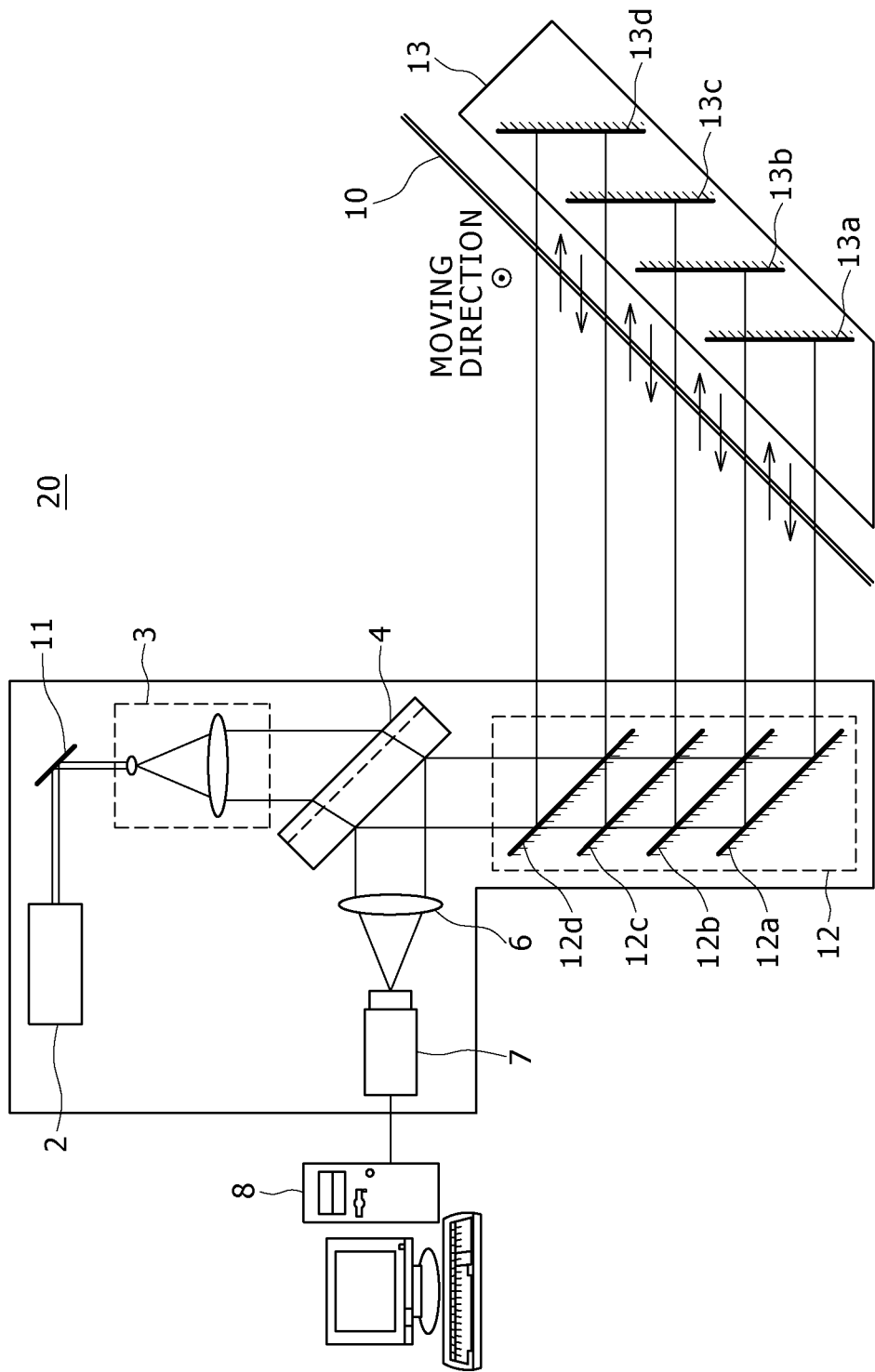
FIG. 5 is a diagram roughly showing a typical configuration of a defect inspection apparatus according to a first embodiment of the present invention.

FIG. 5 is a diagram roughly showing a typical configuration of the defect inspection apparatus 20 according to the first embodiment of the present invention. As shown in FIG. 5, the defect inspection apparatus 20 employs a light source 2, a light reflection mirror 11, a beam expander 3, a wedge plate 4, a first mirror group 12, a second mirror group 13, an image creation lens 6, an imaging section 7 and an analysis section 8. An optical film 10 serving as the object of measurement is placed between the first mirror group 12 and the second mirror group 13. The optical film 10 is moving at a fixed velocity in a direction from a position below the drawing page to a position above the drawing page, that is, in an upward direction relative to the drawing page. As an alternative, the optical film 10 is moving at a fixed velocity in a direction from a position above the drawing page to a position below the drawing page, that is, in a downward direction with respect to the drawing page. It is to be noted that the defect inspection apparatus 20 employs common elements which are also employed in the defect inspection apparatus 1 shown in the diagram of FIG. 1. The common elements are denoted by the same reference numerals as those used in the diagram of FIG. 1 and not explained again in detail in the following description in order to avoid duplications of detailed explanations.

The light reflection mirror 11 is inclined to form an angle determined in advance in conjunction with the direction of incidence of laser light emitted by the light source 2 on the light reflection mirror 11. The light reflection mirror 11 reflects the laser light emitted by the light source 2 to the beam expander 3.

The first mirror group 12 is configured to employ typically first mirrors 12a to 12d. The mirror group 12 splits the circular-shaped wave surface of the incident laser light coming from the wedge plate 4 into a plurality of component wave surfaces each having an approximately rectangular shape and arranges the component wave surfaces in the width direction of the optical film 10.

Figure 6:
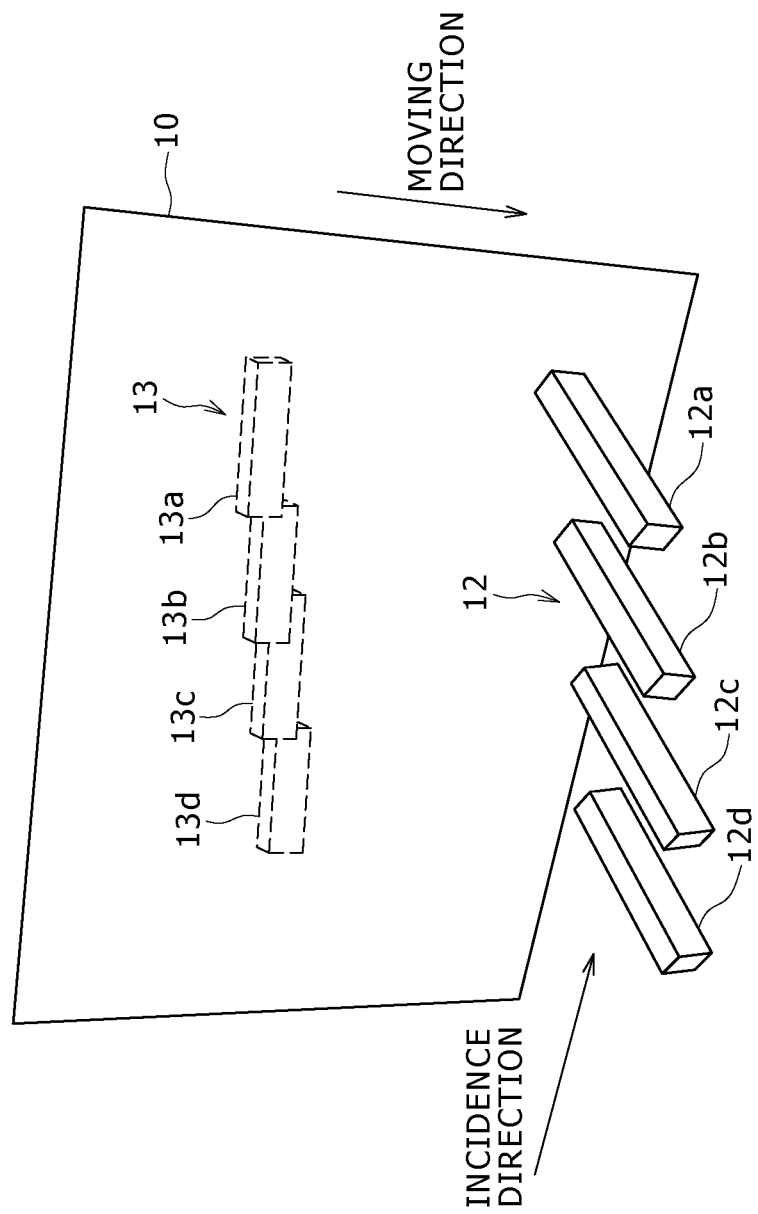
FIG. 6 is a diagram roughly showing a typical layout of first mirrors in accordance with a first embodiment of the present invention.

FIG. 6 is a diagram roughly showing a typical layout of the first mirrors 12a to 12d. The first mirrors 12a to 12d are each inclined to form an angle determined in advance in conjunction with the direction of incidence of laser light emitted by the wedge plate 4 on the first mirror group 12. The first mirrors 12d to 12a are placed at distances, which are increased step by step from mirror to mirror, from the wedge plate 4. The first mirrors 12d to 12a are placed at intervals determined in advance at altitudes which are also increased step by step as their distances from the wedge plate 4 are increased step by step from mirror to mirror. That is to say, the longer the distance from a first mirror to the wedge plate 4, the higher the altitude of the first mirror. Thus, the first mirrors 12a to 12d are placed at such locations that the first mirrors 12a to 12d do not overlap each other.

FIG. 7 is a diagram showing relations between the first mirrors 12a to 12d, the circular wave surface A of incident laser light arriving at the first mirror group 12 to be split by the first mirrors 12a to 12d and the four rectangular wave surfaces A1 to A4 of laser light output by the first mirrors 12a to 12d. The circular wave surface A of the laser light incident on the first mirror group 12 is the cross section of the laser light which is seen from a position on the incidence side of the laser light. As shown at the top of the diagram of FIG. 7, the circular wave surface A can be considered as a wave surface which is composed of the four rectangular wave surfaces A1 to A4. As shown in FIG. 7, the first mirrors 12a to 12d laid out as described above reflect the incident laser light by splitting the four rectangular wave surfaces A1 to A4 enclosed in the circular wave surface A of the laser light into the four rectangular wave surfaces A1 to A4 shown at the bottom on the right side of the diagram of FIG. 7. To put it in detail, the first mirror 12d provided at a location closest to the wedge plate 4 reflects the incident laser light as a laser light beam having the rectangular wave surface A4. By the same token, the first mirror 12c provided at a location relatively close to the wedge plate 4 then reflects the incident laser light as a laser light beam having the rectangular wave surface A3. In the same way, the first mirror 12b provided at a location relatively far away from the wedge plate 4 subsequently reflects the incident laser light as a laser light beam having the rectangular wave surface A2. Likewise, the first mirror 12a provided at a location farthest away from the wedge plate 4 finally reflects the incident laser light as a laser light beam having the rectangular wave surface A1.

The four laser light beams reflected by the first mirrors 12a to 12d respectively to serve as four laser light beams having the rectangular wave surfaces A1, A2, A3 and A4 respectively pass through the moving optical film 10 at different locations adjacently separated from each other in the width direction of the optical film 10. That is to say, the laser light incident on the first mirror group 12 is spread in one direction into the four laser light beams. As a result, the range of inspection of the optical film 10 for existence of a defect can be widened.

The second mirror group 13 is configured to employ typically the second mirrors 13a to 13d mentioned before. As shown in FIG. 6, the second mirrors 13a to 13d are placed at altitudes corresponding to the altitudes of the first mirrors 12a to 12d respectively. In addition, as shown in FIG. 5, the second mirrors 13a to 13d are each oriented in a direction perpendicular to the incidence direction of the incident laser light beams reflected by the first mirrors 12a to 12d respectively. Thus, laser light beams reflected from the second mirrors 13a to 13d propagate to the first mirrors 12a to 12d respectively through the same routes as the incident laser light beams coming from the first mirrors 12a to 12d respectively. That is to say, the four laser light beams obtained as a result of splitting laser light incident on the first mirror group 12 each pass through the same line on the optical film 10 two times.

In addition, the distances between the first mirrors 12a to 12d and the second mirrors 13a to 13d forming mirror pairs in conjunction with the first mirrors 12a to 12d are set at values according to the distances between the first mirrors 12a to 12d and the wedge plate 4. That is to say, the distances between the first mirrors 12a to 12d and the second mirrors 13a to 13d are set at such a value that a laser light beam emitted by the wedge plate 4 returns back to the wedge plate 4 after being reflected by the first mirrors 12a to and the second mirrors 13a to 13d through an optical path having a length determined in advance.

To put it more concretely, the distance between the first mirror 12a placed at a location farthest away from the wedge plate 4 and the second mirror 13a forming a mirror pair in conjunction with the first mirror 12a is set at a smallest value which provides the aforementioned length determined in advance in conjunction with the distance between the first mirror 12a and the wedge plate 4.

Likewise, the distance between the first mirror 12d placed at a location closest to the wedge plate 4 and the second mirror 13d forming a mirror pair in conjunction with the first mirror 12d is set at a largest value which provides the aforementioned length determined in advance in conjunction with the distance between the first mirror 12d and the wedge plate 4.

Thus, the wave surface of incident laser light coming from the wedge plate 4 is split by the first mirrors 12a to 12d into four component wave surfaces of four laser light beams respectively. After the four laser light beams pass through their respective optical paths, the four laser light beams reflected by the second mirrors 13a to 13d respectively again arrive at the first mirrors 12a to 12d respectively. Thus, the four component wave surfaces of four laser light beams are again aligned into one wave surface. Laser light having the aligned wave surface is radiated by the first mirror group 12 back to the wedge plate 4.

As described above, the first mirrors 12a to 12d forming mirror pairs in conjunction with the second mirrors 13a to 13d respectively are used for splitting the wave surface of laser light incident on the first mirror group 12 into typically four component wave surfaces. It is to be noted, however, that the number of component wave surfaces is by no means limited to four. That is to say, it is desirable to properly set the number of component wave surfaces at a value appropriate for the width of the optical film 10 which serves as the object of measurement. For example, the number of component wave surfaces of laser light can be set at an appropriate value which is other than four.

[Operations of the Defect Inspection Apparatus]

Next, operations carried out by the defect inspection apparatus 20 are explained as follows. It is to be noted that the following description explains a case in which the range of measurement is determined on the basis of the width of the optical film 10 and the wave surface of laser light emitted by the wedge plate 4 is split by the first mirror group 12 into eight component wave surfaces. Then, eight laser light beams having the eight component wave surfaces are radiated to the optical film 10.

To put it in detail, laser light emitted by the light source 2 propagates to the beam expander 3 by way of the light reflection mirror 11. The beam expander 3 expands the wave surface of the laser light to a magnitude determined in advance and radiates the laser light to the wedge plate 4 as parallel laser light beams. The laser light incident on the wedge plate 4 passes through the wedge plate 4 and propagates to the first mirror group 12.

As shown in FIG. 8, the wave surface of laser light incident on the first mirror group 12 is split by first mirrors 12a to 12h of the first mirror group 12 into eight component wave surfaces which are then radiated to the optical film 10. The first mirrors 12a to 12h are placed at intervals determined in advance at altitudes which are also increased step by step as their distances from the wedge plate 4 are increased step by step. Thus, the first mirrors 12a to 12h are placed at such locations that the first mirrors 12a to 12h do not overlap each other. As a result, laser light beams reflected by the first mirrors 12a to 12h are arranged in the width direction of the optical film 10, widening the range of inspection of the optical film 10 for existence of a defect.

It is to be noted that, in the typical configuration shown in the diagram of FIG. 8, any particular one of the eight component wave surfaces slightly overlaps a component wave surface adjacent to the particular component wave surface. By slightly superposing any particular one of the eight component wave surfaces on a component wave surface adjacent to the particular component wave surface, even if a defect exists on the optical film 10 at a location on a boundary between any two adjacent component wave surfaces, the defect can be detected.

The component wave surfaces of the laser light beams radiated by the first mirrors 12a to 12h to the optical film 10 pass through the optical film 10 and arrive at respectively second mirrors 13a to 13h. Since the second mirrors 13a to 13h are arranged in a direction perpendicular to the incidence direction of the laser light beams incident on the second mirror group 13, the component wave surfaces of the laser light beams incident on the second mirror group 13 are reflected by the second mirrors 13a to 13h and return to the first mirrors 12a to 12h respectively through the same optical paths as the component wave surfaces of the laser light beams incident on the second mirror group 13. Subsequently, the first mirrors 12a to 12h align the component wave surfaces reflected by the second mirror group 13 to form a single wave surface which is then radiated to the wedge plate 4.

The single wave surface of the laser light incident on the wedge plate 4 is reflected by the first and second surfaces S1 and S2 of the wedge plate 4, being split into two partial wave surfaces. The first surface S1 of the wedge plate 4 is a surface close to the first mirror group 12 whereas the second surface S2 of the wedge plate 4 is a surface close to the beam expander 3. To put it in detail, a part of the laser light reflected from the first mirror group 12 is reflected by the first surface S1 to the image creation lens 6. On the other hand, the rest of the laser light reflected from the first mirror group 12 is not reflected by the first surface S1 to the image creation lens 6. Instead, the rest of the laser light reflected from the first mirror group 12 propagates into the inside of the wedge plate 4 and arrives at the second surface S2. The second surface S2 then reflects the rest of the laser light, which has been reflected from the first mirror group 12, to the image creation lens 6.

A spatial displacement is generated between the two partial wave surfaces emitted from the wedge plate 4. The two partial wave surfaces between which the spatial displacement is generated are superposed on each other in a process carried out by the imaging section 7 to take an image of an interference stripe as described earlier by referring to the diagram of FIG. 3. The imaging section 7 then supplies the image taken by the imaging section 7 as the image of an interference stripe to the analysis section 8 as image data. Subsequently, the analysis section 8 analyzes the image data of the interference stripe.

An image analysis method adopted by the analysis section 8 to serve as a method for analyzing image data is explained by referring to FIG. 9, which is a plurality of diagrams to be referred to in description of an image analysis method, as follows. There is a variety of conceivable image analysis methods. In the case of the first embodiment, an image analysis method using the Fourier transform is adopted. In accordance with the image analysis method using the Fourier transform, the frequency of a spatial carrier is utilized to fetch information on the amplitude of an interference stripe and information on changes in phase.

To put it more concretely, by giving the tilt of an infinitesimal angle between mutually interfering wave surfaces, it is possible to obtain a spatial-carrier stripe expressed by Ex. (5) as a spatial-carrier stripe pattern based on an image of an interference stripe.

$$g(x,y)=a(x,y)+b(x,y)\cos[2\pi(f_{X0}x+f_{Y0}y)+\phi(x,y)] \quad (5)$$

Then, a 2-dimensional Fourier transform is applied to the spatial-carrier stripe pattern in order to obtain a 2-dimensional spatial frequency spectrum which is expressed by Ex. (6) as follows.

$$|G(f_X,f_Y)=A(f_X,f_Y)+C(f_X-f_{0X},f_Y-f_{0Y})+ \\ C^*(-(f_X+f_{0X}),-(f_Y+f_{0Y})) \quad (6)$$

Notation C (fx, fy) used in the above equation denotes a Fourier spectrum of the complex amplitude of light-dark changes in an interference stripe. The Fourier spectrum C (fx, fy) is expressed by Ex. (7) as follows.

$$c(x, y) = \frac{1}{2}b(x, y)\exp[i\phi(x, y)] \qquad (7)$$

Figure 9A:
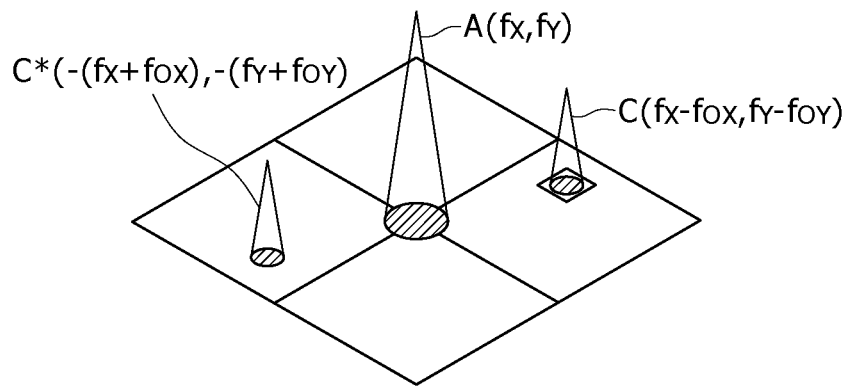
FIG. 9A is a diagram roughly showing typical separation of every spectrum.
Figure 9B:
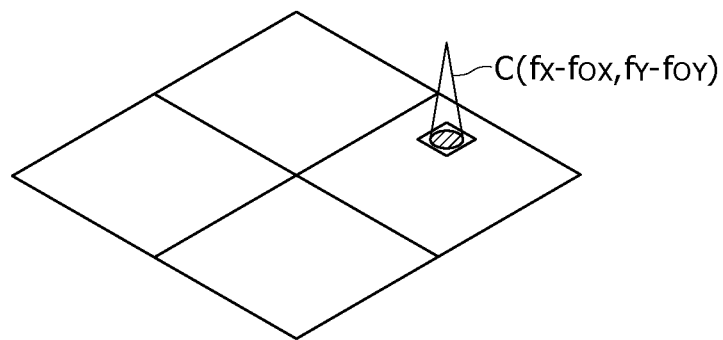
FIG. 9B is a diagram roughly showing a typical predetermined spectrum fetched by adoption of a filtering technique.
Figure 9C:
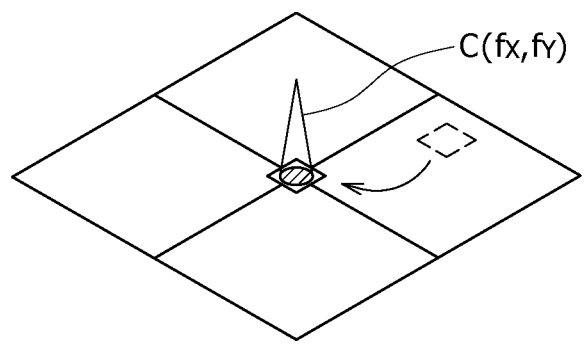
FIG. 9C is a diagram roughly showing typical movement of the fetched spectrum to the point of origin.

In this way, every spectrum is separated by the frequency of the carrier as shown in FIG. 9A. Thus, only the second term of the expression on the right-hand side of Ex. (6) is fetched by adoption of a filtering technique as shown in FIG. 9B which is a diagram roughly showing a typical predetermined spectrum fetched by adoption of a filtering technique. Then, the fetched second term of the expression on the right-hand side of Ex. (6) is moved to the point of origin as shown in FIG. 9C. As a result, the spatial carrier frequencies $f_{x0}$ and $f_{y0}$ are removed and the Fourier spectrum C ($f_x$, $f_y$) can be obtained.

Then, the inverse Fourier transform is applied to the fetched spectrum in order to give a complex amplitude which is expressed by Ex. (7). Thus, it is possible to obtain the amplitude b (x, y) of an interference stripe from the real part of the expression on the right-hand side of Ex. (8) expressing the logarithm of the complex amplitude. In addition, it is also possible to obtain the phase φ (x, y) of the interference stripe from the imaginary part of the expression on the right-hand side of Ex. (8).

$$\log[c(x, y)] = \log\left[\frac{1}{2}b(x, y)\right] + i\phi(x, y) \qquad (8)$$

On the basis of the amplitude information and the phase information obtained in this way of the interference stripe, it is possible to determine whether or not a defect has been generated on the optical film 10.

As described above, in the first embodiment, the wave surface of laser light is split into a plurality of component wave surfaces which are then arranged in the width direction of the optical film 10 in order to widen the range of inspection of the optical film 10 for existence of a defect.

3: Second Embodiment

Next, a second embodiment of the present invention is explained as follows. In the case of the second embodiment, in addition to the first mirror group 12 and the second mirror group 13 which are employed in the first embodiment, a third mirror group 21 and a fourth mirror group 22 are provided in order to propagate laser light through the optical film 10 back and forth more times than the first embodiment.

[Configuration of the Defect Inspection Apparatus]

Figure 10:
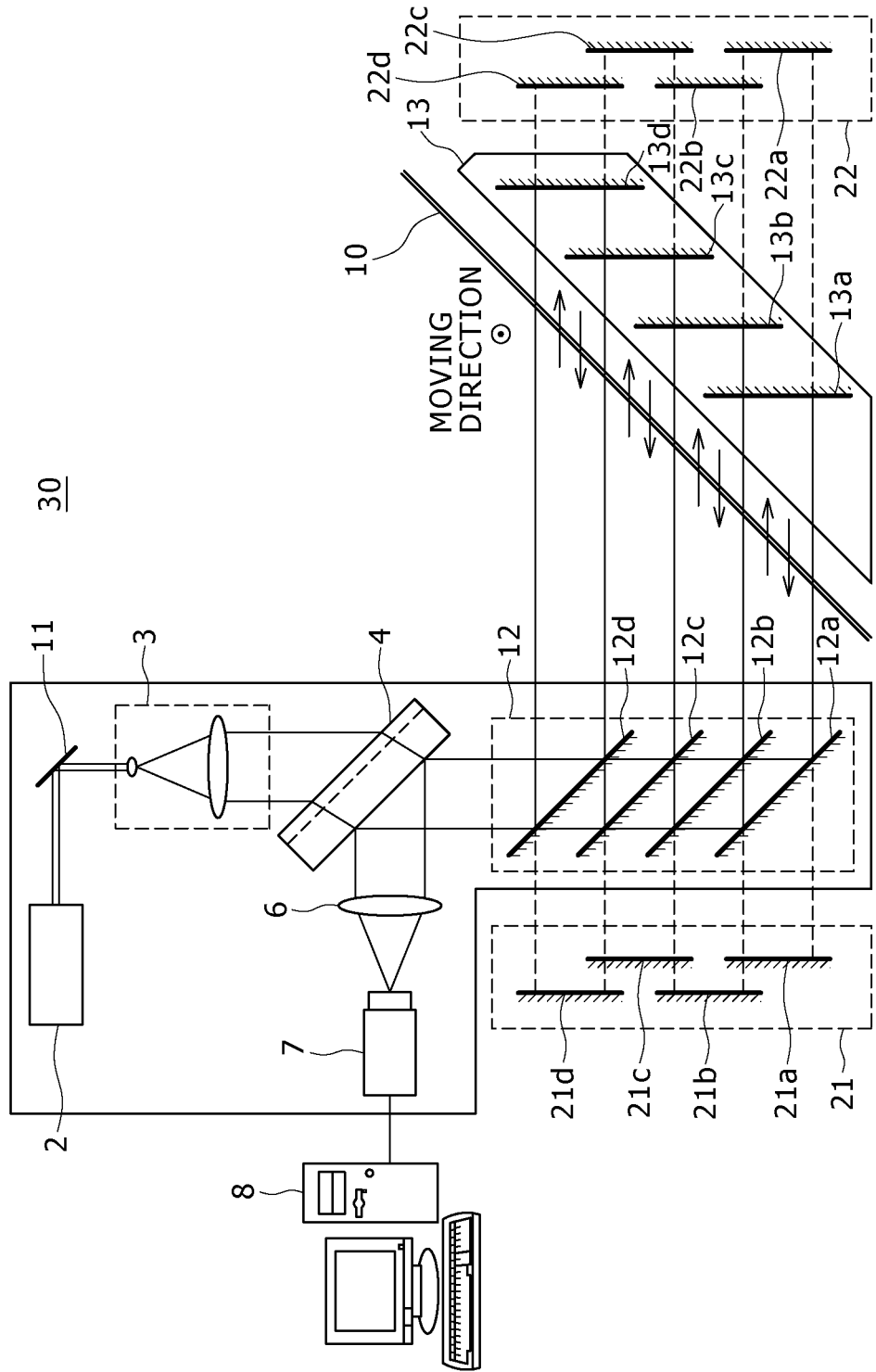
FIG. 10 is a diagram showing a typical configuration of the defect inspection apparatus according to the second embodiment of the present invention.

A typical configuration of the defect inspection apparatus 30 according to the second embodiment of the present invention is explained as follows. FIG. 10 is a diagram showing a typical configuration of the defect inspection apparatus 30 according to the second embodiment of the present invention. As obvious from the above description, the defect inspection apparatus 30 according to the second embodiment is different from the defect inspection apparatus 20 according to the first embodiment in that the defect inspection apparatus 30 also includes the third mirror group 21 and the fourth mirror group 22 in addition to the first mirror group 12 and the second mirror group 13 which are employed in the defect inspection apparatus 20 according to the first embodiment.

It is to be noted that elements employed in the defect inspection apparatus 30 according to the second embodiment shown in the diagram of FIG. 10 to serve as elements identical with their respective counterparts employed in the defect inspection apparatus 20 according to the first embodiment shown in the diagram of FIG. 5 are denoted by the same reference numerals as the counterparts. In addition, the following description does not explain details of the elements employed in the defect inspection apparatus 30 according to the second embodiment shown in the diagram of FIG. 10 to serve as elements identical with their respective counterparts employed in the defect inspection apparatus 20 according to the first embodiment. In this way, it is possible to avoid duplications of descriptions.

The second mirrors 13a to 13d are inclined at such an angle determined in advance that the second mirrors 13a to 13d reflect incident laser light beams propagating from the first mirrors 12a to 12d respectively by way of the optical film 10 to respectively third mirrors 21a to 21d pertaining to the third mirror group 21, which is described below, also by way of the optical film 10.

As described above, the third mirror group 21 is configured to include the third mirrors 21a to 21d which are provided at such upper locations that the third mirrors 21a to 21d are shifted from the first mirrors 12a to 12d respectively in the height direction. That is to say, the third mirrors 21a to 21d are not superposed on the first mirrors 12a to 12d respectively when seen from the location of the optical film 10. In addition, the third mirrors 21a to 21d are inclined at such an angle determined in advance that the third mirrors 21a to 21d reflect incident laser light beams propagating from the second mirrors 13a to 13d respectively to respectively fourth mirrors 22a to 22d pertaining to the fourth mirror group 22, which is described below, by way of the optical film 10.

As described above, the fourth mirror group 22 is configured to include the fourth mirrors 22a to 22d which are provided at such altitudes corresponding to the third mirrors 21a to 21d respectively that the fourth mirrors 22a to 22d are shifted from the second mirrors 13a to 13d respectively in the height direction. That is to say, the fourth mirrors 22a to 22d are not superposed on the second mirrors 13a to 13d respectively when seen from the location of the optical film 10. In addition, the fourth mirrors 22a to 22d are oriented in a direction perpendicular to the incidence direction of incident laser light beams coming from the third mirrors 21a to 21d respectively so that the fourth mirrors 22a to 22d reflect the incident laser light beams coming from the third mirrors 21a to 21d respectively to the third mirrors 21a to 21d respectively by way of the optical film 10.

Thus, the laser light beams incident on the fourth mirror group 22 are reflected by the fourth mirrors 22a to 22d and return to the third mirrors 21a to 21d respectively through the same optical paths as the laser light beams incident on the fourth mirror group 22. The laser light beams reflected by the fourth mirrors 22a to 22d propagates to the third mirrors 21a to 21d respectively by way of the optical film 10 and are reflected by the third mirrors 21a to 21d to the second mirrors 13a to 13d respectively by way of the optical film 10. Finally, the laser light beams are reflected by the second mirrors 13a to 13d back to the first mirrors 12a to 12d respectively by way of the optical film 10.

As described above, in the second embodiment, the third mirror group 21 has the four third mirrors 21a to 21d whereas the fourth mirror group 22 has the four fourth mirrors 22a to 22d. It is to be noted, however, that implementations of the present invention are by no means limited to the second embodiment. That is to say, the number of third mirrors and, thus, the number of fourth mirrors can each be determined in accordance with the number of first mirrors or, thus, the number of second mirrors.

[Operations of the Defect Inspection Apparatus]

Next, operations carried out by the defect inspection apparatus are explained as follows. FIG. 11 is a diagram roughly showing a typical layout of the first to fourth mirrors In order to prevent the explanation from becoming complicated, among the third mirrors 21a to 21d, merely the third mirror 21b is shown in FIG. 11 whereas, among the fourth mirrors 22a to 22d, merely the fourth mirror 22b is shown in FIG. 11.

Laser light emitted by the light source 2 propagates to the beam expander 3 by way of the light reflection mirror 11. The beam expander 3 radiates the laser light to the wedge plate 4 as parallel laser light beams. The laser light incident on the wedge plate 4 passes through the wedge plate 4 and propagates to the first mirror group 12. The first mirrors 12a to 12d splits the wave surface of the laser light incident on the first mirror group 12 into four component wave surfaces and radiates the four component wave surfaces to the optical film 10.

The four laser-light component wave surfaces radiated to the optical film 10 pass through the optical film 10 and are reflected by the second mirrors 13a to 13d respectively. The four laser-light component wave surfaces reflected by the second mirrors 13a to 13d respectively propagate to the third mirrors 21a to 21d respectively by way of the optical film 10 to be reflected by the third mirrors 21a to 21d respectively. The four laser-light component wave surfaces reflected by the third mirrors 21a to 21d respectively propagate to the fourth mirrors 22a to 22d respectively by way of the optical film 10 to be reflected by the fourth mirrors 22a to 22d respectively.

The fourth mirrors 22a to 22d are oriented in a direction perpendicular to the incidence direction of the four incident laser-light component wave surfaces coming from the third mirrors 21a to 21d respectively so that the fourth mirrors 22a to 22d reflect the four incident laser-light component wave surfaces coming from the third mirrors 21a to 21d respectively to the third mirrors 21a to 21d respectively through the same optical paths as the four laser-light component wave surfaces incident on the fourth mirror group 22.

Thus, the four laser-light component wave surfaces incident on the fourth mirror group 22 are reflected by the fourth mirrors 22a to 22d and return to the third mirrors 21a to 21d respectively by way of the optical film 10. The laser light beams reflected by the fourth mirrors 22a to 22d propagate to the third mirrors 21a to 21d respectively by way of the optical film 10 and are reflected by the third mirrors 21a to 21d to the second mirrors 13a to 13d respectively also by way of the optical film 10. Finally, the laser light beams are reflected by the second mirrors 13a to 13d back to the first mirrors 12a to 12d respectively by way of the optical film 10. The first mirrors 12a to 12d align the four laser-light component wave surfaces in order to form a single laser-light wave surface and radiates the single laser-light wave surface to the wedge plate 4.

In the same way as the first embodiment described earlier, the wedge plate 4 splits the single laser-light wave surface radiated thereto into two partial wave surfaces which are then used by the image creation lens 6 to create an interference stripe.

[Detection of Defects on the Optical Film]

Figure 12A:
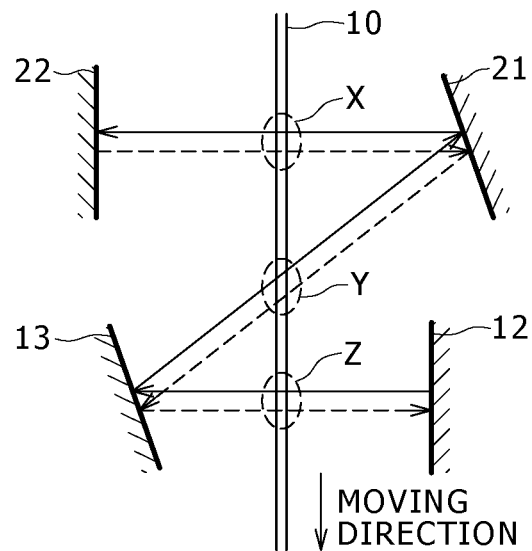
FIG. 12A is an explanatory diagram roughly showing reflection of the laser light.

In the case of the second embodiment of the present invention, in a process of detecting a defect existing on the optical film 10, laser light is emitted to pass through the optical film 10 back and forth a plurality of times. For example, in the case of the second embodiment of the present invention, in addition to the first mirror group 12 and the second mirror group 13 which are employed in the first embodiment, the third mirror group 21 and the fourth mirror group 22 are provided in order to propagate laser light by way of the optical film 10 back and forth more times than the first embodiment. Thus, when laser light is radiated to the optical film 10, the first mirror group 12, the second mirror group 13, the third mirror group 21 and the fourth mirror group 22 propagate the laser light through the optical film 10 back and forth three times as shown in FIG. 12A. As a result, the laser light passes through the same line including spots X, Y and Z on the optical film 10 six times.

Thus, if a cord having a line shape has been generated on the optical film 10 in the horizontal direction with respect to the moving direction of the optical film 10, the curvature of the wave surface of laser light increases when the laser light passes through the optical film 10. As a result, in an operation to observe an interference stripe, the curvature caused by the cord is more emphasized. Accordingly, even if the cord is shallow, the curvature of the wave surface of laser light is emphasized, making it possible to detect a defect caused by the cord.

In addition, let us consider a case in which the thickness of some portions of the TAC film 15 in the optical film 10 changes. Normally, the thickness of the TAC film 15 changes partially in a way different from the way in which a cord is generated on the hard coat layer 16 as a cord having a certain length in a direction parallel to the moving direction of the optical film 10. Thus, even if the wave surface of laser light passes through the optical film 10 back and forth a plurality of times, there is most likely a conceivable case in which the partial change of the TAC film 15 is not detected at all spots existing on the optical film 10 as spots passed through by the wave surface of the laser light.

In the case of the second embodiment of the present invention, the wave surface of laser light is propagated through the optical film 10 back and forth a plurality of times in order to emphasize the curvature of only the wave surface caused by a cord generated on the hard coat layer 16. Thus, it is possible to reduce the effects of thickness changes of the TAC film 15.

Figure 12B:
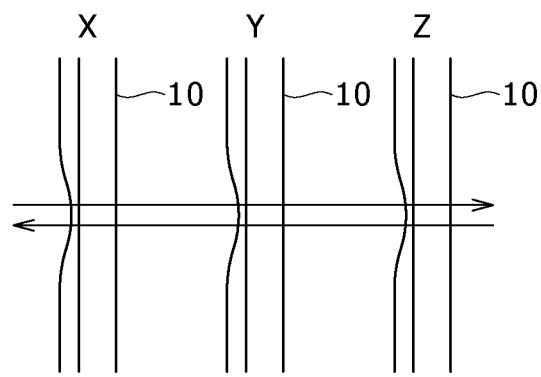
FIG. 12B is an explanatory diagram roughly showing laser light passing through a defective portion of the optical film.

For example, let us consider a case in which a cord has been generated on the hard coat layer 16 of the optical film 10 and the thickness of the TAC film 15 does not change. In this case, at the spots X, Y and Z shown in the diagram of FIG. 12A, the wave surface of laser light passes through a portion at which the cord has been generated. Thus, the wave surface of laser light passes through the portion, at which the cord has been generated, six times as shown in FIG. 12B. FIG. 12B is an explanatory diagram roughly showing the laser light passing through the defective portion.

Figure 12C:
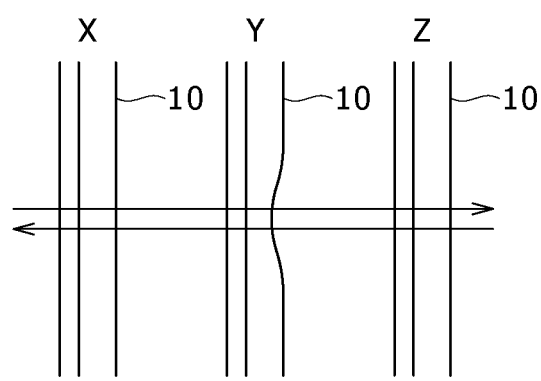
FIG. 12C is an explanatory diagram roughly showing laser light passing through a portion at which the thickness of a TAC film has changed.

As another example, on the other hand, let us consider a case in which no cord has been generated on the hard coat layer 16 of the optical film 10 but the thickness of the TAC film 15 changes at the spot Y shown in the explanatory diagram of FIG. 12A. In this case, at the spot Y, the wave surface of the laser light passes through a portion at which the thickness of the TAC film 15 has changed. Thus, the wave surface of the laser light passes through the portion, at which the thickness of the TAC film 15 has changed, two times as shown in FIG. 12C.

As described above, the wave surface of the laser light passes through the optical film 10 back and forth a plurality of times. In this case, the number of times the wave surface of the laser light passes through a cord portion on the hard coat layer 16 is greater than the number of times the wave surface of the laser light passes through a portion at which the thickness of the TAC film 15 has changed. Thus, when the wave surface of the laser light passes through the cord portion on the hard coat layer 16, the curvature of generated at the interference stripe increases more in comparison with the case of the wave surface of the laser light passing through a portion at which the thickness of the TAC film 15 has changed.

Accordingly, only the curvature increase caused by the cord generated in the hard coat layer 16 is emphasized so that it is possible to reduce the effects of thickness changes of the TAC film 15. As a result, it is possible to prevent a defect caused by a change of the thickness of the TAC film 15 from being detected by mistake.

As described above, in the case of the second embodiment, even if a cord generated on the hard coat layer 16 of the optical film 10 is shallow, the curvature of the wave surface of laser light is emphasized because the laser light propagates through the optical film 10 back and forth a plurality of times, making it possible to detect a defect caused by the cord with an even higher degree of precision than the first embodiment.

In addition, in the case of the second embodiment, laser light passes through the same line on the optical film 10 back and forth a plurality of times. Thus, even if the thickness of the TAC film 15 changes, only the wave-surface curvature caused by a defect existing on the optical film 10 is emphasized. As a result, it is possible to prevent a defect caused by a change of the thickness of the TAC film 15 from being detected by mistake.

As described above, in the case of the second embodiment, the third mirror group 21 and the fourth mirror group 22 are provided. It is to be noted, however, that implementations of the present invention are by no means limited to the configuration of the second embodiment. For example, it is also possible to provide a configuration in which only the third mirror group 21 is added to the first embodiment. In such a configuration, the third mirror group 21 is oriented in a direction perpendicular to the incidence direction of laser light propagating from the second mirror group 13 as laser light incident on the third mirror group 21. Thus, the laser light radiated by the second mirror group 13 to the third mirror group 21 to serve as laser light incident on the third mirror group 21 is reflected by the third mirror group 21 and departs from the third mirror group 21 through the same optical path as the incident laser light. As a result, the laser light passes through the optical film 10 back and forth four times. Accordingly, also in the case of such a configuration, only the wave-surface curvature caused by a defect existing on the optical film 10 is emphasized as is the case with the configuration of the second embodiment in which the laser light passes through the optical film 10 back and forth six times. It is thus possible to prevent a defect caused by a change of the thickness of the TAC film 15 from being detected by mistake.

The first and second embodiments of the present invention have been explained so far. It is to be noted, however, that implementations of the present invention are by no means limited to the configurations of the first and second embodiments described above. That is to say, the configurations of the first and second embodiments can be changed to a variety of modified versions as far as the modified versions fall within a range which does not deviate from spirits of the present invention. In addition, even though each of the first and second embodiments described above employs a TAC film 15 in the optical film 10, implementations of the present invention are by no means limited to this typical configuration. That is to say, a film made from any material can be used provided that the film is capable of transmitting light.

On top of that, each of the first and second embodiments implements a typical configuration which includes a sharing interferometer making use of the wedge plate 4 to serve as an interferometer. It is to be noted, however, that implementations of the present invention are by no means limited to this typical configuration realized by the first and second embodiments. That is to say, an interferometer other than such a sharing interferometer can also be employed as well.

The present application contains subject matter related to that disclosed in Japanese Priority Patent Application JP 2009-204491 filed in the Japan Patent Office on Sep. 4, 2009, the entire content of which is hereby incorporated by reference.

What is claimed is:

1. A defect inspection apparatus comprising:
a light source for emitting laser light;
a mirror group for splitting the wave surface of incident laser light emitted by said light source into a plurality of component wave surfaces, arranging said component wave surfaces to form an array oriented in one direction and aligning said component wave surfaces to form a single wave surface after propagating said laser light through a moving object of measurement;
an interferometer for splitting said single wave surface into two partial wave surfaces and making use of said two partial wave surfaces to create an interference stripe;
an imaging section for taking an image of said interference stripe created by said interferometer; and
an analysis section for detecting a defect existing on the surface of said moving object of measurement on the basis of changes of said image, which has been taken by said imaging section as said image of said interference stripe, with the lapse of time.

2. The defect inspection apparatus according to claim 1 wherein said mirror group propagates said split component wave surfaces through the same line on said object of measurement at least twice.

3. The defect inspection apparatus according to claim 2 wherein said mirror group propagates said split component wave surfaces through the same line on said object of measurement at least four times.

4. The defect inspection apparatus according to claim 1 wherein said interferometer:
has a first surface and a second surface; and
makes use of a wedge plate for splitting incident laser light arriving from said mirror group into laser light reflected by said first surface and laser light not reflected by said first surface but reflected by said second surface.

5. The defect inspection apparatus according to claim 1 wherein said object of measurement is an optical film or a substrate.

6. The defect inspection apparatus according to claim 1 wherein said analysis section analyzes an interference stripe pattern obtained from said image of said interference stripe by adoption of an image processing algorithm determined in advance to detect a detect existing on the surface of said object of measurement.

7. The defect inspection apparatus according to claim 6 wherein said analysis section adopts the Fourier transform as said image processing algorithm.

8. A defect inspection method comprising the steps of:
driving a light source to emit laser light;
driving a mirror group to split the wave surface of incident laser light emitted by said light source into a plurality of component wave surfaces, arranging said component wave surfaces to form an array oriented in one direction and aligning said component wave surfaces to form a single wave surface after propagation of said laser light through a moving object of measurement;

splitting said single wave surface into two partial wave surfaces and making use of said two partial wave surfaces to create an interference stripe;
taking an image of said created interference stripe; and
detecting a defect existing on the surface of said moving object of measurement on the basis of changes of said taken image of said interference stripe with the lapse of time.

* * * * *